(12) United States Patent
Crain et al.

(10) Patent No.: US 11,844,810 B2
(45) Date of Patent: Dec. 19, 2023

(54) ENHANCEMENT OF VACCINE EFFICACY AND ANTIBIOTIC EFFICACY

(71) Applicants: Scott Lowell Crain, Meade, KS (US); David Wayne Farnum, Estherville, IA (US)

(72) Inventors: Scott Lowell Crain, Meade, KS (US); David Wayne Farnum, Estherville, IA (US)

( * ) Notice: Subject to any disclaimer, the term of this patent is extended or adjusted under 35 U.S.C. 154(b) by 0 days.

(21) Appl. No.: 15/991,989

(22) Filed: May 29, 2018

(65) Prior Publication Data

US 2023/0181622 A1 Jun. 15, 2023

Related U.S. Application Data

(62) Division of application No. 15/237,614, filed on Aug. 15, 2016, now abandoned.

(60) Provisional application No. 62/282,907, filed on Aug. 14, 2015.

(51) Int. Cl.

| | | |
|---|---|---|
| A61K 31/716 | (2006.01) | |
| A61K 31/715 | (2006.01) | |
| A23K 50/10 | (2016.01) | |
| A23K 50/20 | (2016.01) | |
| A23K 50/30 | (2016.01) | |
| A23K 50/40 | (2016.01) | |
| A23K 20/163 | (2016.01) | |
| A23K 20/195 | (2016.01) | |
| A61P 11/00 | (2006.01) | |
| A61K 38/00 | (2006.01) | |
| A23K 20/10 | (2016.01) | |
| A61K 45/06 | (2006.01) | |
| A23K 20/20 | (2016.01) | |
| A23K 20/147 | (2016.01) | |
| A61K 33/30 | (2006.01) | |

(52) U.S. Cl.
CPC ............ *A61K 31/716* (2013.01); *A23K 20/10* (2016.05); *A23K 20/147* (2016.05); *A23K 20/195* (2016.05); *A23K 20/30* (2016.05); *A23K 50/10* (2016.05); *A23K 50/30* (2016.05); *A61K 31/715* (2013.01); *A61K 33/30* (2013.01); *A61K 38/00* (2013.01); *A61K 45/06* (2013.01)

(58) Field of Classification Search
CPC .... A61K 31/716; A61K 33/30; A61K 31/715; A23K 20/30; A23K 50/10; A23K 20/10
See application file for complete search history.

(56) References Cited

U.S. PATENT DOCUMENTS

| | | | |
|---|---|---|---|
| 3,579,635 A | * | 5/1971 | Raun ...................... C07H 17/08 514/30 |
| 4,020,158 A | | 4/1977 | Ashmead |
| 4,167,564 A | | 9/1979 | Jensen |
| 4,774,089 A | | 9/1988 | Ashmead |
| 4,863,898 A | | 9/1989 | Ashmead |
| 5,066,498 A | | 11/1991 | McCauley |
| 5,162,369 A | | 11/1992 | Ashmead |
| 5,882,685 A | | 3/1999 | Ashmead |
| 6,214,337 B1 | | 4/2001 | Hayen |
| 2009/0227535 A1 | * | 9/2009 | Courie, Jr. ............. A61K 35/74 514/54 |
| 2012/0202770 A1 | | 8/2012 | Elvebo |
| 2013/0216586 A1 | | 8/2013 | LeBrun |

OTHER PUBLICATIONS

Zaheer et al, Frontiers in Microbiology, vol. 4, Article 133, May 2013, pp. 1-14.*
Greene, L. W., et al. "Performance and carcass quality of steers supplemented with zinc oxide or zinc methionine." Journal of animal science 66.7 (1988): 1818-1823.*
Cockcroft, Peter D. "Antimicrobial Selection in Cattle Practice." Bovine Medicine 3 (Apr. 24, 2015): 225-237. (Year: 2015).*
Doster, Alan R. "Bovine atypical interstitial pneumonia." Veterinary Clinics: Food Animal Practice 26.2 (2010): 395-407. (Year: 2010).*
Andersen, Niels Møller, et al. "Inhibition of protein synthesis on the ribosome by tildipirosin compared with other veterinary macrolides." Antimicrobial agents and chemotherapy 56.11 (2012): 6033-6036. (Year: 2012).*
Boothe, et al., Macrolides, Merck Veterinary Manual, 2017, 7 pages. Retrieved on Sep. 20, 2017, from: http://www.merckvetmanual.com/pharmacology/antibacterial-agents/macrolides.
Country Feeds Grower Finisher Pig Feed Product Sheet, 1 page, Retrieved on Sep. 20, 2017, from: https://www.nutrenaworld.com/product/country-feeds-grower-finisher-pig-feed.
Country Feeds Starter-Grower Pig Feed Product Sheet, 1 page. Retrieved on Sep. 20, 2017, from: https://www.nutrenaworld.com/product/country-feeds-starter-grower-pig-feed.
Country Feeds Whole Life Pig Feed Product Sheet, 1 page. Retrieved on Sep. 20, 2017, from Internet at https://www.nutrenaworld.com/product/country-feeds-whole-life-pig-feed.
Macrolides, American Academy of Veterinary Pharmacology and Therapeutics, Veterinary Antibiotic Monographs, 2007, 24 pages. Retrieved on Sep. 21, 2017, from: http://c.ymcdn.com/sites/www.aavpt.org/resource/resmgr/imported/macrolides.pdf.
Mineral Needs Chart: Bags, 2 pages. Retrieved on Sep. 20, 2017, from the Internet at www.purinamills.com/purinamills/media/PDF/Cattle/Mineral%20Events/PurinaCattle_Mineral-Charts-updated_050916.
Nutrebeef Cattle Mineral Product Sheet, 1 p., downloaded from the Internet at https://www.nutrenaworld.com/product/nutrebeef-cattle-mineral on Sep. 20, 2017.
Nutrebeef Cubes Product Sheet, 1 p., downloaded from the Internet at https://www.nutrenaworld.com/product/nutrebeef-cubes on Sep. 20, 2017.

(Continued)

*Primary Examiner* — Bethany P Barham
*Assistant Examiner* — Peter Anthopolos
(74) *Attorney, Agent, or Firm* — Mintz, Levin, Cohn, Ferris, Glovsky and Popeo, P.C.

(57) ABSTRACT

Disclosed herein are compositions and methods for modulating a macrolide antimicrobial, modulating an immune function, increasing the effectiveness of an antibiotic, and/or increasing the number and effectiveness of alveolar macrophages in treating a vertebrate animal. The method comprises feeding to the animal a feed composition comprising (1, 3), (1, 6), beta-glucans and optionally mannans to increase the number of alveolar macrophage cells, and administering a macrolide antibiotic to the animal.

28 Claims, 7 Drawing Sheets

(56) References Cited

OTHER PUBLICATIONS

Nutrebeef Grower/Finisher Feed Product Sheet, 1 p., downloaded from the Internet at https://www.nutrenaworld.com/product/nutrebeef-grower-finisher-feed on Sep. 20, 2017.
NutreBeef Hi-Mag Mineral Product Sheet, 1 p., downloaded from the Internet at https://www.nutrenaworld.com/product/nutrebeef-hi-mag-mineral on Sep. 20, 2017.
Nutrebeef Starter Creep Feed Product Sheet, 1 p., downloaded from Internet at https://www.nutrenaworld.com/product/nutrebeef-starter-creep-feed on Sep. 20, 2017.
Nutrebeef Transition Feed Review Sheet, 1 p., downloaded from Internet at https://www.nutrenaworld.com/product/nutrebeef-transition-feed on Sep. 20, 2017.
Purina Accuration Grower Product Sheet, 8 pp., downloaded from Internet at www.purinamills.com/cattle-feed/products/detail/purina-accuration-grower on Sep. 20, 2017.
Purina Accuration Range Liquid 10% Fat Product Sheet, 8 pp., downloaded from Internet at www.purinamills.com/cattle-feed/products/detail/purina-accuration-range-liquid-10-fat on Sep. 20, 2017.
Purina Precon Complete, Features & Benefits Sheet, 8 pp., downloaded from Internet at www.purinamills.com/cattle-feed/products/detail/purina-precon-complete on Sep. 20, 2017.
Purina Stress Care 5 Supplement Features & Benefit Sheet, 8 pp., downloaded from Internet at www.purinamills.com/cattle-feed/products/detail/purina-stress-care-5-supplement on Sep. 20, 2017.
Purina Wind and Rain Storm All Season, 8 pp., downloaded from Internet at www.purinamills.com/cattle-feed/products/detail/purina-wind-and-rain-storm-all-season on Sep. 20, 2017.
Purina Wind and Rain Storm Fescue, 8 pp., downloaded from Internet at www.purinamills.com/cattle-feed/products/detail/purina-wind-and-rain-storm-fescue on Sep. 20, 2017.
Purina Wind and Rain Storm Fly Control Product Sheet, 8 pp., downloaded from Internet at www.purinamills.com/cattle-feed/products/detail/purina-wind-and-rain-storm-fly-control on Sep. 20, 2017.
Purina Wind and Rain Storm Hi-Mag Product Sheet, 8 pp., downloaded from Internet at www.purinamills.com/cattle-feed/products/detail/purina-wind-and-rain-storm-hi-mag on Sep. 20, 2017.
Purina Wind and Rain Storm Mineral Tub Product Sheet, 9 pp., downloaded from Internet at www.purinamills.com/cattle-feed/products/detail/purina-wind-and-rain-storm-mineral-tub on Sep. 20, 2017.
Purina® Accuration® Range Supplement 33 Product Sheet, 1 p., downloaded from Internet at www.purinamills.com/2.purinamills.com/media/Images/Products/Purina-Accuration-Range-Supplement-33.pdf?ext =.pdf on Sep. 20, 2017.
Purina® Wind and Rain® Storm® Cattle Minerals Spreadsheet, 1 p., downloaded from Internet at www.purinamills.com/2.purinamills.com/media/Images/Products/Wind-Rain-Storm-Analysis-Non-Med.pdf?exis=.pdf on Sep. 20, 2017.
Purina Accuration Range Supplement 33, 1 page, Retrieved on Sep. 20, 2017, from: https://www.purinamills.com/cattle-feed/products/detail/purina-accuration-range-supplements.
Bhattacharyya, et al., Oxidative Stress: An Essential Factor in the Pathogenesis of Gastrointestinal Mucosal Diseases, Physiol. Rev., 2014, pp. 329-354, vol. 94, No. 2.
Bello-Klein, et al., Oxidative Stress Influence in the Development of Pulmonary Arterial Hypertension, Chapter 14, Biochemistry of Oxidative Stress, 2016, pp. 213-226.
Evelson, et al., Inhaled Particulate Matter Leads to Myocardial Dysfunction, Chapter 18, Biochemistry of Oxidative Stress, 2016, pp. 275-285.
Fantone, et al., Role of Oxygen-Derived Free Radicals and Metabolites in Leukocyte-Dependent Inflammatory Reactions, Review Article, Dept. of Pathology, Univ. of Michigan, 1982, pp. 397-418, vol. 107, No. 3.
Otero-Losada, et al., Oxidative Stress and Antioxidants in Experimental Metabolic Syndrome, Chapter 24, Biochemistry of Oxidative Stress, 2016, pp. 375-390.
Ketola, et al., Monensin is a Potent Inducer of Oxidative Stress and Inhibitor of Androgen Signaling Leading to Apoptosis in Prostate Cancer Cells, Molecular Cancer Therapeutics, 2010, pp. 3175-3185, vol. 9, No. 12.
Veriprime, Reduce Clinical Signs of AIP Using Amino Acid Chelates, 2017, 2 pages, vol. 4.

\* cited by examiner

| | | Mortality | Lung Lesions |
|---|---|---|---|
| Group 1: Antibiotic; Beta-glucan; | APP Serotype 5 | 4% | 12% |
| Group 2: Antibiotic; | APP Serotype 5 | 8% | 17% |
| Group 3: | APP Serotype 5 | 32% | 28% |
| Group 4: no treatment | No Challenge | | |

| | Control | Feed Combination | Improvement |
|---|---|---|---|
| Day 10 WBC Count | 9.8 | 10.8 | 10% |
| Lymphocyte Count (acquired immunity) | 6.4 | 6.8 | 6% |
| Monocytes (tissue macrophages) | 0.34 | 0.48 | 41% |

| Change in IBR Titer | Cattle Fed the feed composition of the present inventions | Control cattle |
|---|---|---|
| 3 weeks post vaccination all cattle | 17 | 8 |
| 3 weeks post vaccination cattle arrived with IBR titer | 175 | 35 |

FIG. 13

ENHANCEMENT OF VACCINE EFFICACY AND ANTIBIOTIC EFFICACY

CROSS-REFERENCE TO RELATED APPLICATIONS

This application is a divisional of U.S. application Ser. No. 15/237,614, filed Aug. 15, 2016, which claims the benefit of and priority to U.S. Provisional Application No. 62/282,907, filed Aug. 14, 2015, entitled ENHANCEMENT OF ANTIBIOTIC EFFICACY, the entire content of which is hereby incorporated by reference.

FIELD OF THE INVENTION

The present invention relates to the field of veterinary medicine and more specifically to prevention, management and treatment of health disorder or diseases of farm animals.

BACKGROUND OF THE INVENTION

One of the primary objectives in the industry is herd health management. Bovine respiratory disease (BRD) is the most common and costly problem encountered in stocker or feedlot calves. BRD, also called "shipping fever," also accounts for major economic losses to the producer by reducing average daily gain, feed efficiency, and overall performance of beef calves.

BRD is a respiratory disease complex that occurs most often within 14 days after calves have been weaned. The weaning process is the most stressful time for calves. At that time, calves are usually castrated, extensively handled, commingled, and shipped to other locations, resulting in tremendous exposure to the many infectious agents that cause BRD. Stress also has a negative impact on the immune system of calves, causing them to be even more vulnerable to "shipping fever". Other factors which increase the risk of BRD include, but are not limited to, movement through sale yards, poor body condition, and transport over long distances. On arrival at final destinations, calves are often dehydrated, exhausted, and have a reduction in appetite. As a result, it is not uncommon for many calves to develop severe bronchopneumonia and even die from "shipping fever".

There are several types of infectious agents involved in this complex respiratory disease, including Bovine Viral Diarrhea (BVD), Infectious Bovine Rhinotracheitis (IBR), Bovine Respiratory Syncytial Virus (BRSV), and Parainfluenza Type-3 Virus (PI-3). Exposure to these viruses can cause severe damage to the airways (respiratory tract) of calves, creating opportunities for bacteria to then settle in the lungs.

The most common bacteria found in the lungs of calves with BRD include *Mannheimia haemolytica* and *Pasteurella multocida*. *Histophilu somnus* may also be involved and often causes severe damage to the heart muscles. Vaccines are also available for these bacteria. Another bacteria-type organism that is being found more often in the past few years is *Mycoplasma bovis*. This organism not only causes severe pneumonia but also swollen, painful joints in calves.

Symptoms of BRD usually develop within 14 days after the weaning process. Signs can be variable since there may be one or more viruses and bacteria involved in this disease complex. Early clinical signs usually include: depression, anorexia, dull eyes, and fever. Clinical signs later in the course of the disease include: rapid/labored breathing, droopy ears, coughing, diarrhea, sudden death, staggering, and nasal discharge.

Early recognition and treatment of calves with BRD usually improves their outcome and overall performance. Treatment options vary, but most involve the use of antibiotics specifically designed to treat calves with pneumonia. In addition, some producers and veterinarians will also administer anti-inflammatory drugs for fever or vitamins. Response to therapy is usually observed within 24 hours and a successful outcome is closely related to early recognition of BRD clinical signs.

Nevertheless, improvements in vaccine efficacy and immune modulation are needed, as no new vaccines or antibiotics are expected to become available in the near future.

SUMMARY OF THE INVENTION

Disclosed herein is a feed composition comprising an effective amount of beta-glucans, including any known beta-glucan, beta-glucans that have the various linkages (e.g., 1, 3; 1, 4; and 1, 6), and combinations of the various beta-glucans. For example, some embodiments relate to compositions and uses of (1, 3), (1, 6), beta-glucans alone or in combination. The beta-glucans can be isolated or purified from their source, such as from the microorganism that produced them. The feed compositions can be non-human animal feed compositions. For example, for any non-human vertebrate animal, including mammals, birds, fish, etc. For example, the composition can be composition for a bovine, porcine, equine, caprine, ovine, hircine, canine, feline, avian, fish, and the like.

In some embodiments, the feed composition further comprises at least one bulking agent. In some embodiments, the feed composition further comprises mannans. In some embodiments, the amount of the (1, 3), (1, 6), beta-glucans is from about 15% to about 16% by weight of the composition. Some embodiments relate to a composition and methods of using such compositions that comprise a ration of (1,3)/(1,6) beta-glucans. For example the ratio can range from about 1:15 to about 15:1, from about 1:10 to about 10:1, from about 1:7 to about 7:1, from about 1:5 to about 5:1, from about 1:3 to about 3:1, from about 1:2 to about 2:1 and to about 1:1, or any value or sub range with any of those ranges.

In some embodiments, the feed composition further comprises a bulking agent. Any suitable bulking agent can be used. For example, the bulking agent can include zinc, for example, but not limited to, Zinc Acetate, Zinc Acexamate, Zinc Aspartate, Zinc Chloride, Zinc Citrate, Zinc Difumarate Hydrate, Zinc Gluconate, Zinc Methionine, Zinc Monomethionine, Zinc Murakab, Zinc Orotate, Zinc Oxide, Zinc Picolinate, Zinc Pyrithione, Zinc Sulfate, Zinc Sulphate, Zincum Aceticum, Zincum Gluconicum, Zincum Metallicum, Zincum Valerianicum, elemental Zinc and hydrates and/or the combinations thereof. In some embodiments, the zinc is of an amount of no less than 13,000 ppm by weight.

In some embodiments, the (1, 3), (1, 6), beta-glucans of the feed composition can be derived from a yeast. In some embodiments, the mannans of the feed composition are derived from a yeast. In some embodiments, the yeast is Saccharomyces cerevisiae yeast extract, yeast culture, hydrolyzed yeast, and/or a combination thereof. In some embodiments, the (1, 3), (1, 6), beta-glucans and/or mannans are isolated from the yeast. In preferred embodiments, the (1, 3), (1, 6), beta-glucans and/or mannans are not added to the composition as live yeast. In especially preferred embodiments, the (1, 3), (1, 6), beta-glucans and/or mannans are isolated from the yeast.

In some embodiments, the feed composition further comprises protein and/or fiber. In some embodiments, the protein is crude protein. In some embodiments, the fiber is crude fiber. In some embodiments, the crude protein is of no less than about 10% by weight of the feed compositions. In some embodiments, the crude fiber is of no less about 16% by weight of the feed composition.

In some embodiments, disclosed herein is a method for treating a vertebrate animal, the method compromising feeding the animal an effective amount of the feed composition described herein above to increase a number of alveolar macrophage cells, followed by administering a macrolide antibiotic to the animal.

In some embodiments, the feed composition is fed to the animal for a period of at least about five days before administering the macrolide antibiotic. In some embodiments the composition is fed 1, 2, 3, 4, 5, 6, 7 or more days prior to the antibiotic. In some embodiments the composition is fed on the same days as the antibiotic, and/or after receipt of the antibiotic. In some embodiments, the compositions are provided at the same time as the antibiotic.

In some embodiments, a macrolide antimicrobial of the animal in treatment is modulated.

In some embodiments, an immune function of the animal is modulated.

In some embodiments, the effectiveness of the antibiotic is increased, and wherein the feeding of the feed composition comprises about at least 5 days feeding period prior to a stressful event. In some embodiments the feed compositions is provided about 1, 2, 3, 4, 5, 6, 7 or more days prior to a stressful event. In some embodiments the composition is fed on the same days as the stressful event, and/or after the stressful event. In some embodiments, the compositions are provided at the same time as the stressful event.

In some embodiments, a number and/or size of lesions in the animal's lung is reduced, and wherein the feeding of the feed composition comprises about at least 5 days feeding period prior to a stressful event. In some embodiments the feed compositions is provided about 1, 2, 3, 4, 5, 6, 7 or more days prior to a stressful event. In some embodiments the composition is fed on the same days as the stressful event, and/or after the stressful event. In some embodiments, the compositions are provided at the same time as the stressful event.

In some embodiments, the effective amount of the feed composition comprises an amount of (1,3), (1,6) beta-glucan ranging from about 50 mg to about 300 mg per animal per day, wherein the animal is cattle.

In some embodiments, the effective amount of the feed composition comprises an amount of (1,3), (1,6) beta-glucan ranging from about 7 mg to about 13 mg per lb. per day, and wherein the animal is swine.

In some embodiments, disclosed herein is a method of managing the health of an animal, the method comprising feeding an effective amount of the feed composition described herein to the animal and concurrently administering an antibiotic to the animal.

In some embodiments, the method of managing the health of an animal is carried out during a receiving period of between about five days and about 30 days or any value or sub range there between. In a preferred embodiment, the method is carried out during a period of about 10 days and about 25 days or any value or sub range there between. In an especially preferred embodiment, the period is about twenty one days.

In some embodiments, the health of the animal is managed during, prior to, or post a stressful event.

In some embodiments, disclosed herein is a method for supplementing a dust pneumonia treatment of an animal, the method comprising feeding to an animal an effective amount of the feed composition described herein above, administering a macrolide antibiotic to the animal, and running the animal in a dust pneumonia yard.

Some embodiments relate to compositions comprising a feed composition as described herein in combination with at least one feed supplement, feed additive, or feed material. In some embodiments the supplement, additive or material comprises an ionophore, for example, one or more of monensin, lasalocid, laidlomycin salinomycin and narasin. Commerical products that can be included with the compositions described herein include Rumensin® (monensin), Bovitec® (lasalocid), Skycis® (narasin), Cattlyest® (laidlomycin propionate). The proprietary and other inophores, supplements and additives can be utilized according their known amounts for use with animals. Other additives/supplements can include, for example, Phosphoglycolipid antibiotics (e.g., flavophospholipol), bambermycins, virginiamycin, zinc bacitran, and the like. Other products can include, for example, products by Purina such as their Wind and Rain® products (e.g., All Season™, Fescue™, Fly Control™, and Hi Mag™), Accuration® products (e.g., Starter, Finisher, Backgrounder, Grower, Steakmaker, etc.), Precon® (e.g., Complete), Stress Care™ 5 Supplement; Cargill products such as for example, Nutrena®, ACCO Feeds®, Agway®, Right Now® minerals, Safe Choice®, Nature Wise® (poultry and avians),Country Feeds® poultry feed, NutreBeef® (Creep, transition, textured feed, cattle cubes, summer mineral, summer mineral with fly control, Hi-mag mineral, winter mineral, etc.), Country Feeds® for pigs (e.g., Pig Starter Grower, Pig Grower Finisher, Whole Life Pig Feed), Aquaxcel®; and other known feeds, supplements and additives. The above combinations can be utilized in any of the methods described herein.

In some embodiments any macrolide antibiotic can be utilized or be the target of the methods and compositions. The macrolides can include or be 14, 15 or 16-membered macrolides antibiotics. Non-limiting examples include tylosin (e.g.,Tylan®), tilmicosin (e.g., Micotil®), tulathromycin (e.g.,Draxxin), gamithromycin (e.g., Zactran®;), tildipirosin (e.g., Zuprevo®), azithromycin, erythromycin (e.g., Erythro-200), aureomycin, clarithromycin, oleandomycin, roxithromycin, telithromycin, josamycin, mideacamycin, miocamycin, rokitamycin, spiramycin, tildipiromycin, and tylvalosin.

Some embodiments relate to methods of reducing the amount of a macrolide antibiotic usage with a given animal or group of animals. For example, some embodiments relate to treatment protocols and feed or treatment combination products that include any of the compositions described herein for use in connection or in combination with a reduced amount of an antibiotic. For example, the amount of a macrolide antibiotic can be reduced by anywhere from 1% to about 35% (or any value or subrange there between) when used with the compositions and methods as described herein. Such methods can reduce antibiotic burden on the environment. For example, if the approved or standard amount or dosage of antibiotic in a veterinary or animal husbandry setting is 8-15 mg/kg, then the amount might be reduced by 1% to 35% of the numbers in that range (e.g., reduced by 0.08 to 2.8 mg/kg-0.15 to 5.25 mg/kg). Similarly, the frequency of administration may be reduced, for example, for multiple times per day to fewer times per day or to every other day or to every third day, etc. The skilled artisan will know the amounts/dosages for macrolides for each type of animal as well as frequency and can calculate the reductions. Examples of some dosages and frequency can be found in the Merck Veterinary Manual, which is incorporated herein by reference in its entirety (The Merck Veterinary Manual. Whitehouse Station, NJ :Merck & Co., Inc.). Other examples, can be found in product listings and brochures (for any of the Purina and Cargill products references above, all of which are incorporated herein by reference in their entireties), and in information found in the "Macrolides" monograph (The United States Pharmacopeia. The National Formulary. Rockville, Md, :United States Pharmacopeial Convention, Inc. 2007., which is incorporated herein by reference in its entirety).

DETAILED DESCRIPTION

In the current environment, maximization of current treatments is important, especially when new antibiotics or vaccines are not likely to be developed/approved anytime soon. In other words, improved vaccine efficacy and immune modulation is sought after in the industry. For example, cattle pulled once have 50% lower chance of making "choice."

Mass medication (metaphylaxis) with long acting antibiotics given to all calves, on arrival, is another prevention strategy that has become more common. Extensive research has indicated that the number of BRD cases in treated calves, on arrival, is greatly reduced. In addition, treated calves will have improved average daily gain, feed efficiency, and overall performance.

These factors support the use of metaphylaxis and have proven to be cost effective. Several Glucan, mannan products are available in the market for feeding cattle. Beta-glucans and mannans induce immune cell proliferation. Beta-glucans are taken up in the Peyer's Patches in the gut of an animal and are utilized by the immune system.

Beta-Glucans

E.g., (1, 3), (1, 6), beta-glucan

The isolation or purification, for example, from their source organism (e.g., yeast organism) of a beta-glucan such as a (1, 3) and/or a (1, 6), beta-glucan product can be an important consideration. (1, 3), (1, 6), beta-glucan travels through the stomach and is delivered to immune cells through the Peyer's Patches. Beta-glucans bind to specific receptor sites on immune cells. Immune cells digest the (1, 3), (1, 6), beta-glucan and transport it throughout the lymphatic system. Neutrophils, macrophages, NK cells, and eosinophils all have receptor sites for Beta-glucans. The presence of Beta-glucans attached to immune cells primes the immune system causing proliferation of innate immune cells, and complement, and cytokines.

Mannan-Oligosaccharide (MOS)

Sow diets supplemented with MOS also aims to the improving the health of the sows. For example, a healthy sow produces good quality colostrum and spreads less harmful bacteria in the environment where she gives birth and raises the piglets. It has been reported that there is a significant increase in colostrum production and colostrum quality with MOS. Those changes in colostrum quality and quantity likely explain a reduced pre-weaning mortality and a higher litter size and litter weight at weaning and can thereby help to better protect the piglet from disease, thus improving piglet survival. Mortality of young piglets was reduced when MOS was supplemented in the diets of the sow. Keeping the mortality of young piglets to a minimum is important from an economical as well as from an animal welfare point of view.

The next critical phase in a piglet's life is the time of weaning, when it is separated from the sow. The change from milk to solid feed leads to changes in the intestinal microflora and structure and thus presents a higher risk of intestinal problems. Two meta-analyses involving a total of 123 comparisons, concluded that performance was better in piglets fed MOS-supplemented feed. The data also indicated that piglets, which were particularly challenged during this transition phase (showing a slower growth rate due to the challenge), responded particularly well to MOS supplements. Positive performance effects with MOS were also reported in later production phases; however, those effects appear to be smaller than in the very young animals.

The first trial reported with MOS was with young bull calves. Newman et al. noted improved intake and subsequently better growth rates. The health status of young calves is one of the most important factors contributing to growth and performance. Diarrhea in young calves is a major issue in the dairy sector. The cause can be viral or bacterial; however, E. coli is often involved. As MOS can bind E. coli, it can modify and help to improve the composition of the intestinal microflora. This resulted in a reduction in faecal E. coli counts and improvements in faecal score in calves fed MOS. These improvements were coupled with an increase in concentrate (dry feed) intake and better performance. In addition to the changes in the gut, several authors also noticed improvements in respiratory health, which can also contribute to better performance. Conversely, one trial reported no effects on live weight gain despite increased feed intake. Higher live weight gain, similar to that gained with the use of antibiotics, has been achieved following supplementation of milk replacer with MOS.

Dairy cows fed with MOS had better immune protection against rotavirus and were able to pass some of this protection on to their calves. The transfer of immunity from the cow to the calves is critical in order to protect the calf from many different diseases.

In the yeast cell wall, mannan oligosaccharides are present in complex molecules that are linked to the protein moiety. There are two main locations of mannan oligosaccharides in the surface area of *Saccharomyces cerevisiae* cell wall. They can be attached to the cell wall proteins as part of —O and —N glycosyl groups and also constitute elements of large α-D-mannanose polysaccharides (α-D-Mannans), which are built of α-(1,2)- and α-(1,3)-D-mannose branches (from 1 to 5 rings long), which are attached to long α-(1,6)-D-mannose chains. This specific combination of various functionalities involves mannan oligosacharides-protein conjugates and highly hydrophilic and structurally variable 'brush-like' mannan oligosaccharides structures that can fit to various receptors of animal digestive tracts, and to the receptors on the surface of bacterial membranes, impacts these molecules bioactivity. Mannan oligosacharides-protein conjugates are involved in interactions with the animal's immune system and as result enhance immune system activity. They also play a role in animal antioxidant and anti-mutagenic defense. MOS is included in diets for horses, dogs, cats, rabbits and birds by feed manufacturers, mainly due to its benefits for their health. MOS as a nutritional supplement offers a natural approach to support the microflora and thus improve overall health, well-being and longevity.

Intestinal immune cells (Peyer's Patches) have been shown to be able to absorb or uptake the beta-glucans and to initiate the immune responses based thereof, which is further shown to be highly responsive to yeast mannans and beta-glucans derived, extracted or purified from whole yeasts. The result is elevated immune signaling and recruitment of macrophages and other immune cells to the intestine to counter anticipated pathogenic challenges.

In one embodiment, a supplement with *Saccharomyces cerevisiae* cell wall extract that contains both Beta-glucan and mannan oligosaccharides are obtained from commercial manufacturers.

In one embodiment, the feed composition of the present invention is a blend of prebiotics, and (1, 3)/(1, 6) Beta-glucans and optionally mannans. In some aspects, the (1, 3)/(1, 6) Beta-glucans and/or mannans are extracted or derived and/or purified under controlled conditions from the cell walls of yeasts. In some aspects, the yeasts are food grade yeast *Saccharomyces cerevisiae*. In some aspects, the yeasts are provided from hydrolyzed yeast, yeast extract, yeast culture, and/or the combinations thereof. In some aspects, when the derived (1, 3)/(1, 6) Beta-glucans and/or mannans are not purified or entirely purified, the feed composition of the present invention comprises hydrolyzed yeast, yeast extract, yeast culture, and/or the combinations thereof In some embodiments, the (1,3), (1,6) beta-glucan is of an amount of from about 10% to about 20% by weight of the feed composition. In a preferred embodiment, the amount ranges from about 12% to about 18% by weight of the feed composition. In an especially preferred embodiment, the amount is of from about 15% to about 16% by weight of the feed composition.

In one embodiment, the feed composition further comprises zinc. In some aspects, the zinc of the feed composition includes, but is not limited to, Zinc Acetate, Zinc Acexamate, Zinc Aspartate, Zinc Chloride, Zinc Citrate, Zinc Difumarate Hydrate, Zinc Gluconate, Zinc Methionine, Zinc Monomethionine, Zinc Murakab, Zinc Orotate, Zinc Oxide, Zinc Picolinate, Zinc Pyrithione, Zinc Sulfate, Zinc Sulphate, Zincum Aceticum, Zincum Gluconicum, Zincum Metallicum, Zincum Valerianicum, Zn, and/or the combinations thereof.

Given that the percentage of elemental zinc varies by the forms of the compositions, for example, approximately 23% of zinc sulfate consists of elemental zinc, 220 mg of zinc sulfate only provides for 50 mg of elemental zinc. Therefore, the amount of zinc refers herein to the amount of element zinc a composition or compound can provide.

In one embodiment, the feed composition also contains protein, fat, fiber, and/or the combination thereof. In some aspects, the feed composition containscrude protein of no less than 10% by weight. In some aspects, the feed composition contains crude fat of no less than 0.3% by weight. In some aspects, the feed composition contains crude fiber of no more than 12.5% by weight. In some aspects, the feed composition contains zinc of no less than 13,000 ppm by weight.

In one embodiment, the effective amount of the feed composition comprises an amount of (1,3), (1,6) beta-glucan ranging from about 50 mg to about 300 mg per animal per day, for example when fed to cattle. In some aspects, the amount of (1,3), (1,6) beta-glucan ranges from about 40 mg to about 360 mg per animal per day. In some aspects, the effective amount of the feed composition, e.g., for steers and heifers, ranges from about 1.5 g to about 3 g per head per day. In some aspects, the effective amount of the feed composition, e.g., for steers and heifers, ranges from about 1.2 g to about 3.6 g per head per day. In some aspects, the effective amount of the feed composition is about 3 g per head per day. In some aspects, the effective amount of the feed composition ranges from about 2.4 g to about 3.6 g per head per day.

In one embodiment, the effective amount of the feed composition comprises an amount of (1,3), (1,6) beta-glucan ranging from about 7 mg to about 13 mg per lb. per day, for example when fed to swine. In some aspects, the amount of (1,3), (1,6) beta-glucan ranges from about 5.6 mg/lb. to about 15.6 mg/lb. per day. In some aspects, the effective amount of the feed composition ranges from about 100 g to about 200 g per ton per day. In some aspects, the effective amount of the feed composition ranges from about 80 g to about 240 g per ton per day.

In one embodiment, the feed composition of the present invention should be stored in a cool dry protected location in original packaging and protect from humidity and excessive heat, with the product container closed tightly when not in use to avoid contamination.

In one embodiment, the feed composition of the present invention is fed to an animal at 1.5 grams per head of the animal per day during a receiving period. In some aspects, the receiving period is between about five days and about 30 days. In some aspects, the receiving period is between about 10 days and about 25 days. In some aspects, the receiving period is about 21 days.

The feed composition can also be fed to an animal any time it faces or will face stress. In some aspect, the stress comes from extreme environmental conditions. In some aspects, the feed composition is fed concurrently with the antibiotic to the animal during the receiving period. In some aspects, the feed composition is fed to the animal prior to or post a stressful event. As used herein, the term "concurrently" refers to feeding the feed composition and administering the antibiotic within 96 hours of each other. In some aspects, the feeding of the feed composition and the administering of the antibiotic are within 72 hours of each other, 48 hours of each other, 36 hours of each other, within 24 hours of each other, within 12 hours of each other, within 10 hours of each other, within 8 hours of each other, within 6 hours of each other, within 4 hours of each other, within two hours of each other, within 1 hour of each other. In some aspects, the feeding of the feed composition and the administering of the antibiotics are at substantially the same time.

In one embodiment, the feed composition of the present invention is fed to a vertebrate animal. In some aspects, the feed composition of the present invention is fed to farm animals or livestock including, but not limited to bovine, swine, equine, caprine, ovine and fish.

In one embodiment, the feed composition of the present invention is fed to household animals or pets including, but not limited to, dog, cats, rabbits, horses and birds. In some aspects, the feed composition is fed to the above described animals under the veterinary care.

In some embodiments, the feed composition of the present invention is safe for use in all food-producing animals and animal feeds. In some embodiments, the feed composition of the present invention is a quality source of functional nutrients and yeast cell wall components. In some embodiments, the feed composition of the present invention is not a live yeast product and is stable in pelleted feeds. In some embodiments, the feed composition of the present invention is can be used concurrently with any feed antibiotics (no combination approval required) and/or water medications. No withdrawal is required prior to slaughter.

Effects of the Feed Composition

Beta-glucans have been shown to enhance the immune system of animals. Mannans have been shown to bind to intestinal bacterial pathogens and are a substrate for beneficial lactobacilli, improving the intestinal flora. Many of the newer antibiotics used to treat Bovine Respiratory Disease (BRD) are macrolides. This class of antibiotic is dependent on the alveolar macrophage. Beta-glucans increase both the number and activity of macrophages. In side by side pen comparisons, cattle supplemented with Beta-glucan increased macrophages 12% over untreated cattle.

Macrolide antibiotics are strongly accumulated within phagocytic cells; they have a preferential granular/lysosomal location and, in general, retain their antibacterial activity inside the cells. Their intracellular activity has been investigated using various in vitro cellular models and some animal models.

The effect of macrolides on intracellular pathogens may be classified according to their main cellular localization; such as phagolysosomes, phagosomes, or cytosol. Animal models suggest a synergistic interaction between polymorphonuclear leukocytes and macrolides.

Macrolides concentrate intracellularly, which results in the advantage of a targeted delivery system, bringing active drug to infection sites by the phagocytes. While the uptake of macrolides into PMN cells and macrophages is completed within 30 minutes, the uptake of macrolides into cells continues for at least 24 hours. Macrolides are released slowly from macrophages resulting in the release of antimicrobial into the extracellular medium. Macrophages are represented by pulmonary epithelial lining fluid (PELF) and bronchoalveolar lavage (BAL) cells. The Beta-glucans in the feed composition of the present invention increase the number and activity of macrophages (BAL and PELF). For example, cattle fed with Beta-glucans experienced a 12% increase in macrophages.

Figure 1:
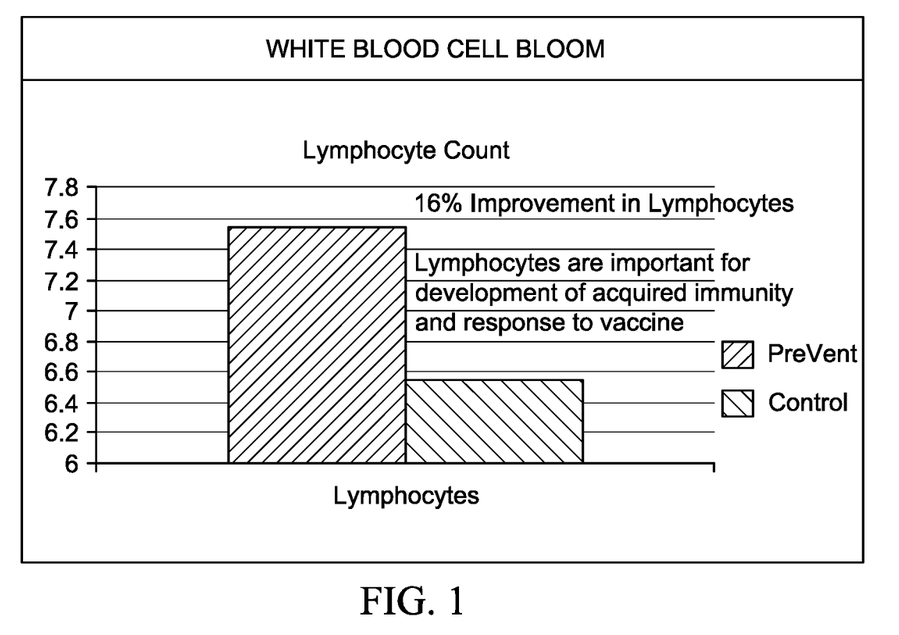
FIG. 1 shows a comparison chart demonstrating that the Cattle fed with PreVent showed a 16% increase in lymphocyte count compared to controls.
Figure 2:
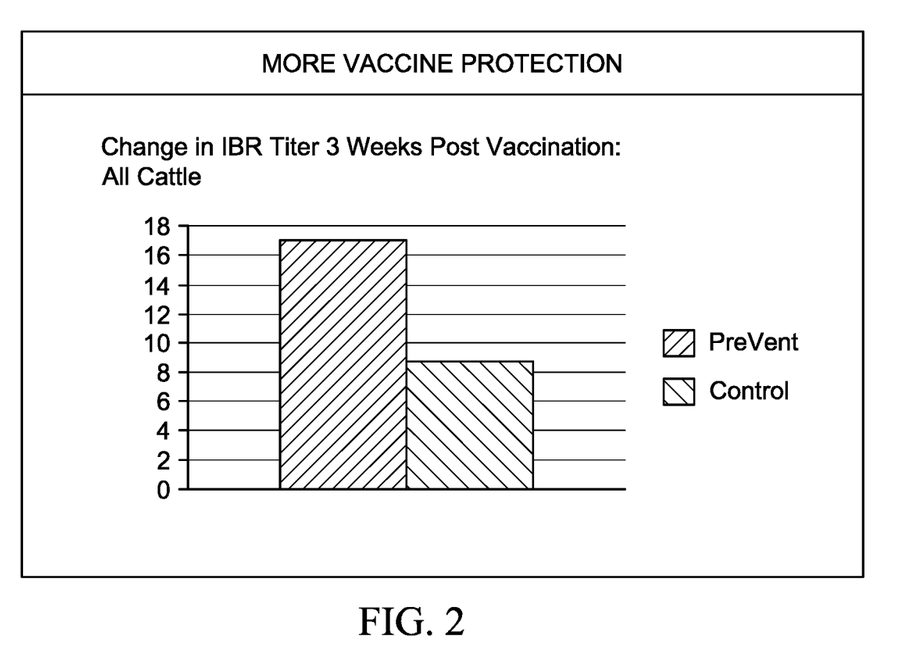
FIG. 2 shows a comparison chart demonstrating that lymphocytes are important for acquired immunity and cattle fed PreVent had higher titers to infectious bovine rhinotracheitis (IBR).
Figure 3:
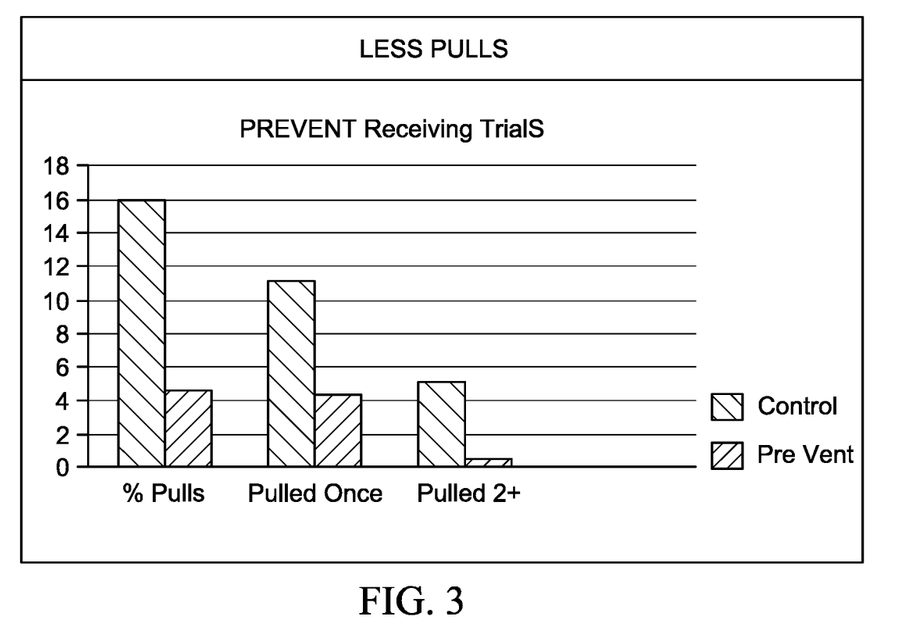
FIG. 3 shows a comparison chart demonstrating that the cattle fed with PreVent had lower morbidity (pulled once) and a lower relapse rate (pulled 2+) than cattle in the control groups.

The feed composition of the present invention further provides the benefits of increasing vaccine efficacy and immune modulation in the animals fed with the feed composition. The above described benefits can be provided in the animals fed with the feed composition of the present invention prior to any administering of antibiotics to the animals. The above described benefits can also be provided in the animals fed with the feed composition of the present invention during or post any administering of antibiotics to the animals. In one study, PreVent, an embodiment of the feed composition of the present invention was fed to one group of cattle. As shown in FIG. 1, cattle fed with PreVent showed a 16% increase in lymphocyte count compared to control group of cattle not fed with PreVent. As shown in FIG. 2, cattle fed with PreVent had higher titers to infectious bovine rhinotracheitis (IBR) compared to the control group cattle not fed with PreVent, measured three (3) weeks post the vaccination. The higher titer results indicate improved vaccination protection and efficacy for the animal. Also as shown in FIG. 3, cattle fed with PreVent not only had lower morbidity (as illustrated in the pulled once bar), but also a lower relapse rate (as illustrated in the pulled 2+ bar) than the control group of cattle not fed with PreVent.

EXAMPLE 1

Prophylactic Treatment

The effect of the feed composition of the present invention on swine is studied in this example. One hundred head of 60 # pigs were split into 4 groups. Three of the four groups were challenged with *Actinobacillus pleuropneumonias* serotype 5 (APP Serotype 5). One Group was receiving Beta Glucan Supplement. Three days prior to challenge we injected two of the three groups with Draxxin® antibiotic. The percentage of lung lesion was recorded in all pigs that died during the trial period. On day 12 all surviving pigs were sacrificed and the percent of lung lesions was recorded.

Figure 4:
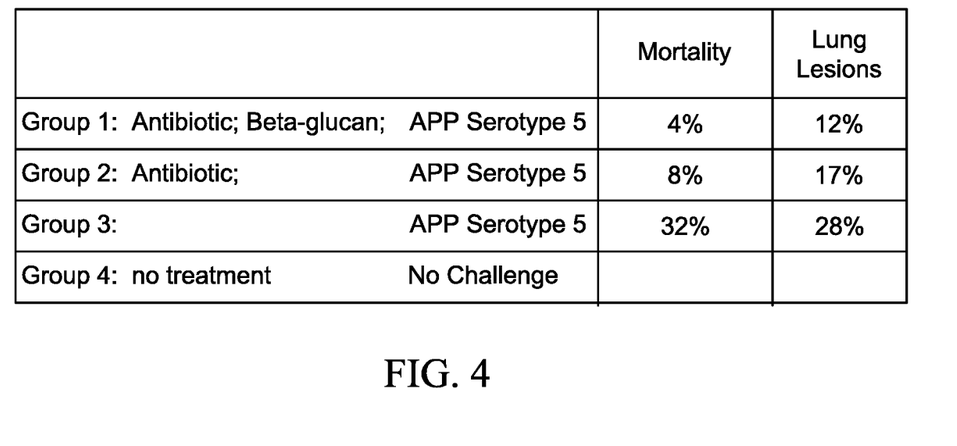
FIG. 4 shows a comparison demonstrating that pigs treated with a macrolide antibiotic and PreVent had lower mortality and fewer lung lesions that pigs that were un treated or only treated with a macrolide antibiotic.
Figure 5:
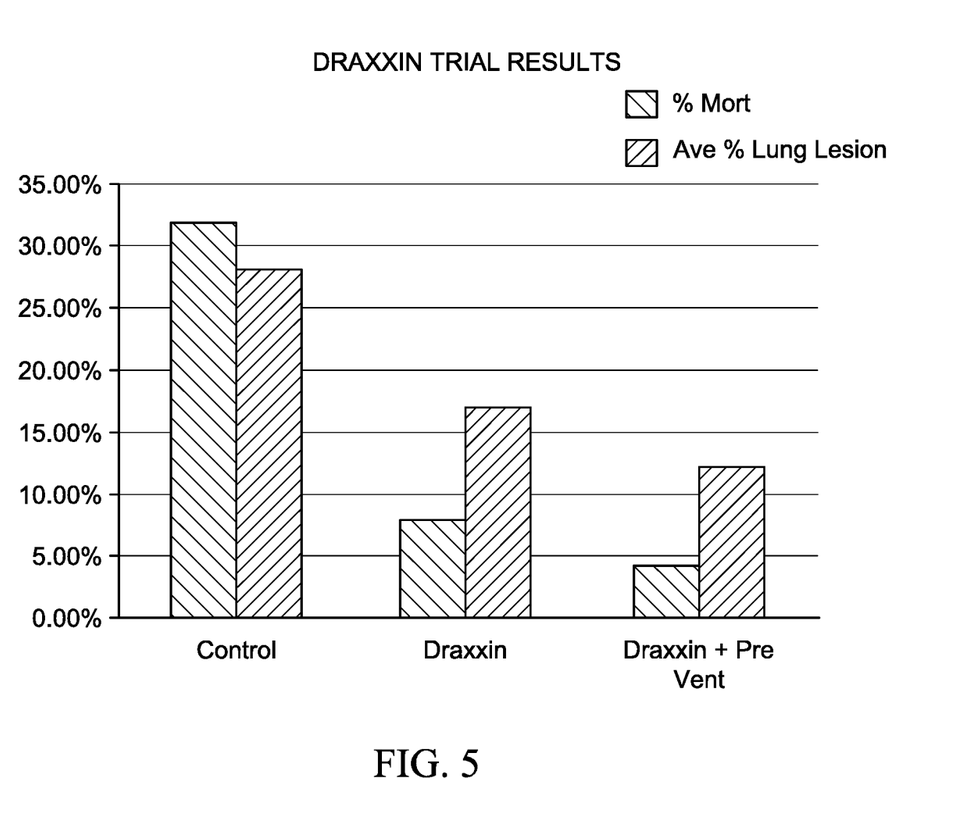
FIG. 5 shows a comparison chart also demonstrating that pigs treated with a macrolide antibiotic and PreVent had lower mortality and fewer lung lesions that pigs that were un treated or only treated with a macrolide antibiotic.
Figure 6:
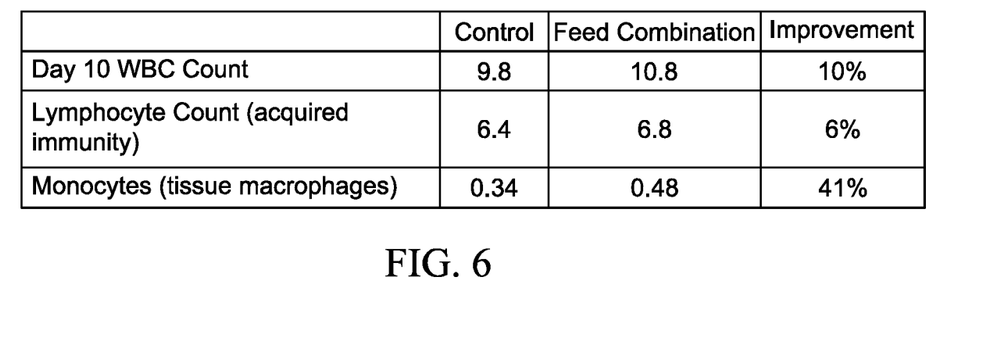
FIGS. 6-9 show comparison charts demonstrating cattle fed with PreVent had improved total white blood cell count, increased lymphocytes and increased monocytes.
Figure 7:
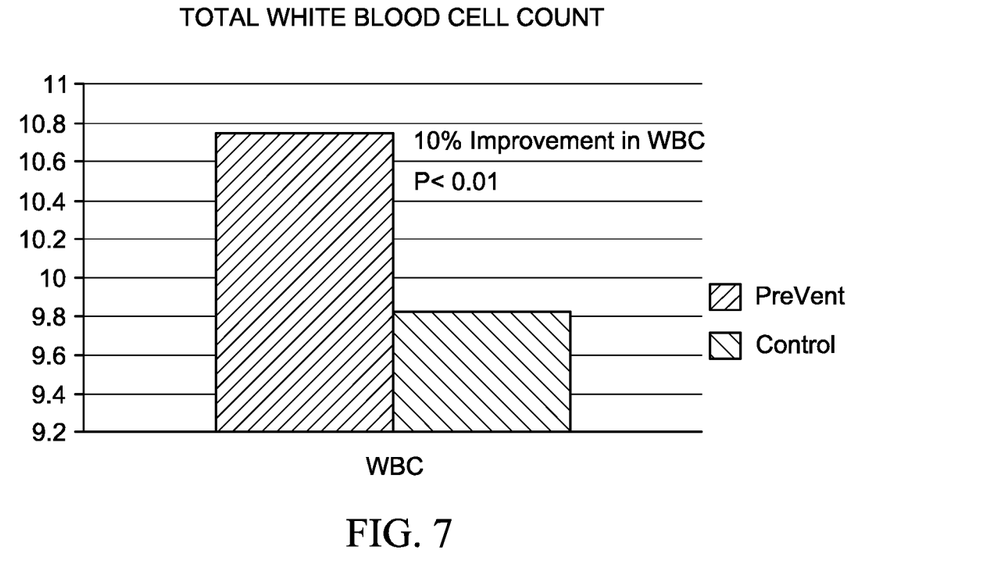
Figure 8:
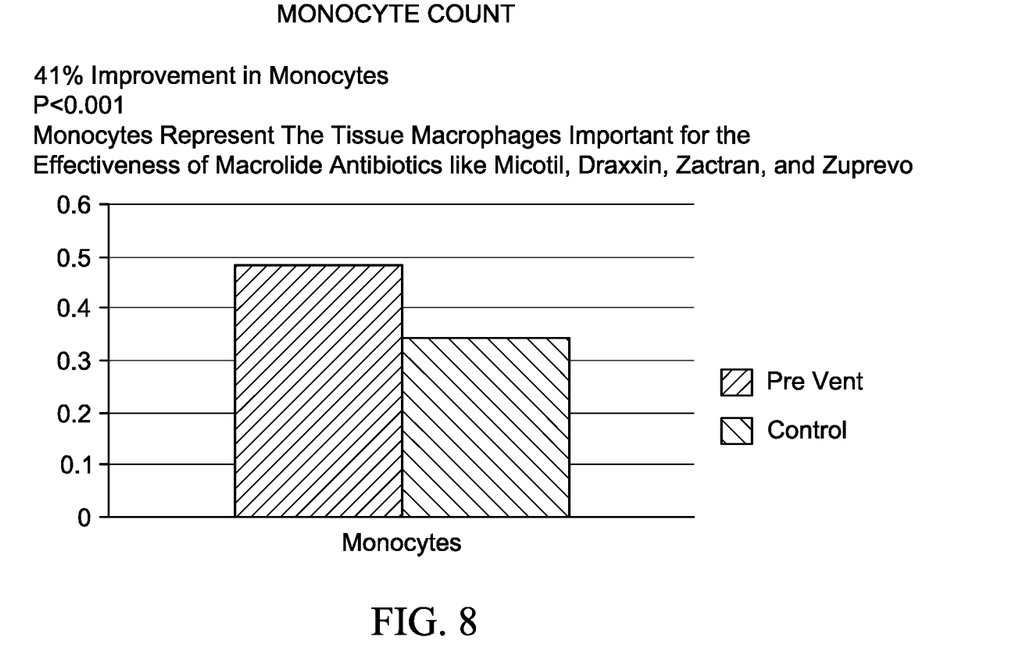
Figure 9:
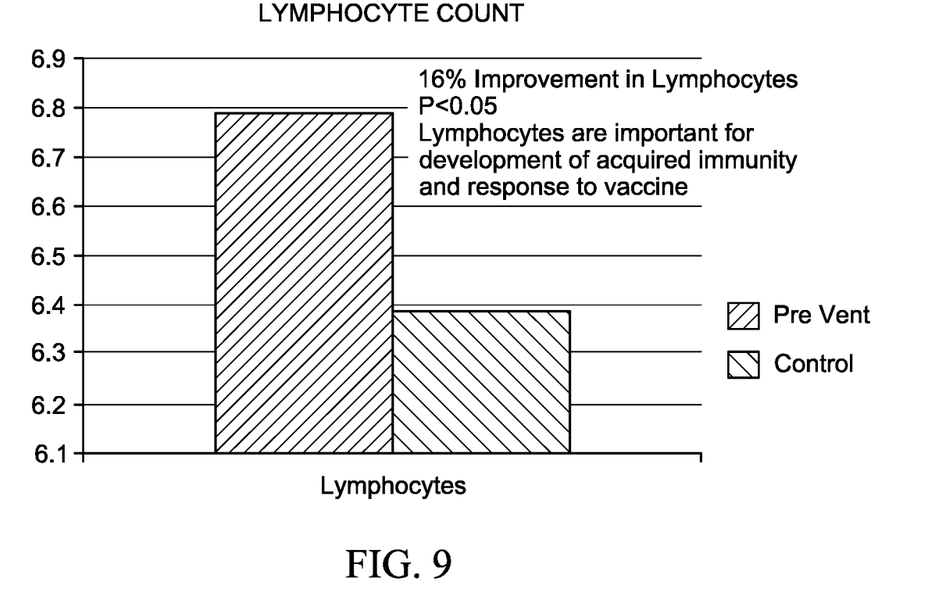

As shown in FIGS. 4-5, pigs treated with a macrolide antibiotic and PreVent had both lower mortality and fewer lung lesions compared to the control group of pigs that were not treated, or only treated with a macrolide antibiotic.

EXAMPLE 2

Ongoing CHMN Receiving Trial

The effect of the feed composition of the present invention on cattle is studied in this example. We split loads of cattle into control and treatment with the feed composition of the present invention. On day ten we collected blood from 15 head in each group to counts of the White Blood Cell (WBC), lymphocytes, and monocytes using the results from the blood work.

As shown in FIGS. 6-9, cattle fed with PreVent had improved total white blood cell count, increased lymphocytes and increased monocytes. In each repetition, the cattle given the feed composition of the present invention had statistically significant Improvement in white blood cells. Here, the increased level of the count of lymphocyte indicates the improved acquired immunity from vaccination; and the similarly increased level of monocytes count indicates the elevated level of tissue macrophages important for the effectiveness of the medication of various antibiotics including, but not limited to, Micotil, Draxxin, Zactran, and Zuprevo.

EXAMPLE 3

Response to Infectious Bovine Rhinotracheitis (IBR) Virus Vaccine

The effect of improved responsiveness to vaccination by use of the feed composition of the present invention on cattle is studied in this example. Cattle were split on receiving and paired serum samples for IBR were collected to measure the response to receiving vaccine. Cattle arrived with a negative and positive IBR titers were given the feed composition of the present invention.

Figure 10:
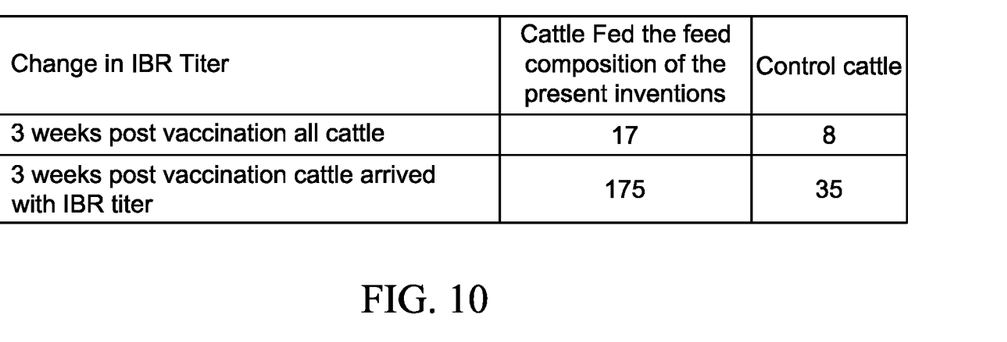
FIGS. 10-12 show comparison charts demonstrating that the IBR titer from vaccine was greater in cattle fed with PreVent during the receiving period than the titer increase in control cattle. The difference was greatest in those cattle that arrived with titers indicating prior exposure to IBR.
Figure 11:
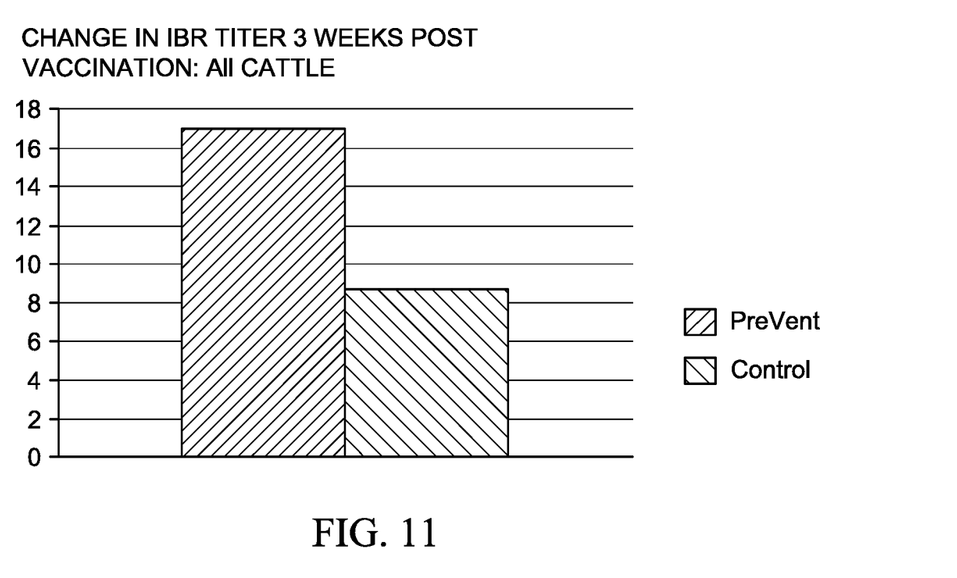
Figure 12:
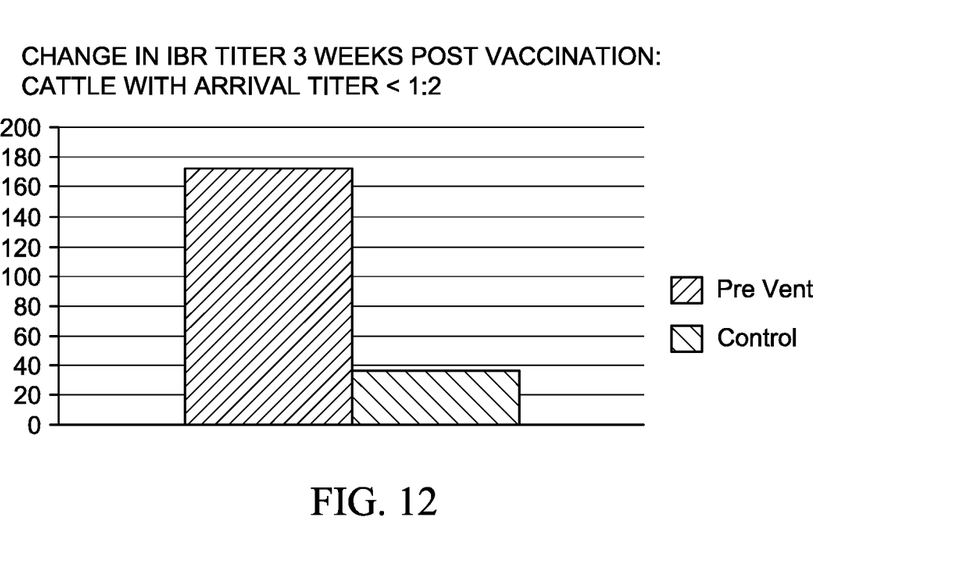
Figure 13:
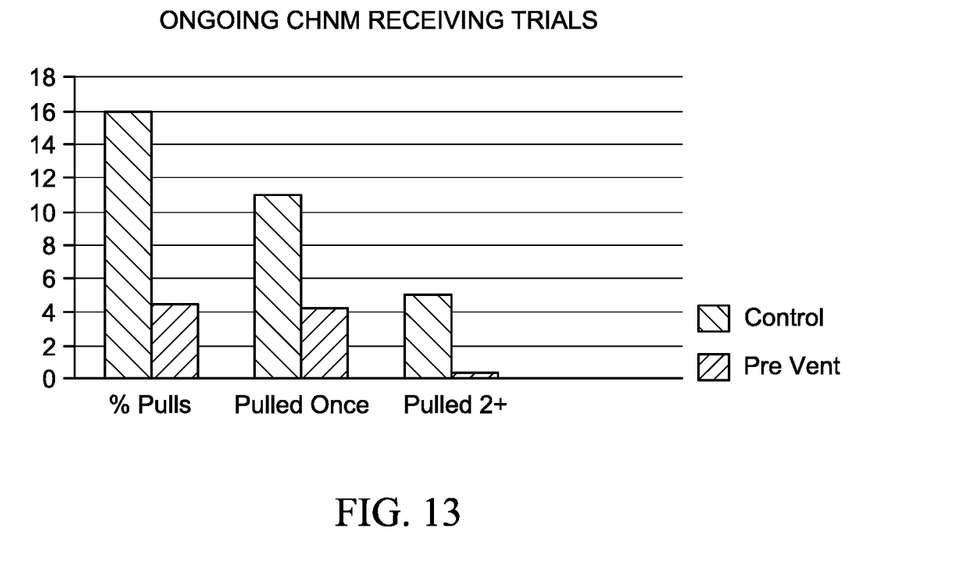
FIG. 13 shows a comparison chart demonstrating that cattle fed with PreVent had lower morbidity (pulled once) and a lower relapse rate (pulled 2+) than cattle in the control groups.

As shown in FIGS. 10-12, the IBR titer from vaccine was greater in cattle fed with PreVent during the receiving period compared to the IBR titer increase in control group of cattle not fed with PreVent. Here, the figures also show that cattle received with a negative IBR titer and fed with the feed composition of the present invention had a 477% improved response to vaccine; while cattle received with a positive IBR titer and fed the feed composition of the present invention had a 200% improved response to vaccine. The difference was greatest in those cattle that arrived with titers indicating prior exposure to IBR. In other words, cattle fed with the feed composition of the present invention show improved vaccine efficacy.

EXAMPLE 4

Inflammatory Response after LPS Challenge

The effect on the immune system by use of the feed composition of the present invention on cattle is studied in this example. Lipopolysaccharide (LPS) is the major component of the outer membrane of Gram-negative bacteria. LPS induces a strong response from normal animal immune systems. Omptin proteases rely upon binding of lipopolysaccharide for activity. Omptins, a family of proteases embedded in the outer membrane of Gram-negative bacteria that cleave various substrates, have been linked with pathogenesis in several gram negative enterobacteria. Following challenge with LPS, cattle will display increased sickness behavior beginning at 0.5 hours, with heifers on average displaying less sickness behavior than bulls. A febrile response can be observed in all animals following LPS administration, with a maximum response observed from 4 to 5.5 hours. The average rectal temperature response will tend to be greater in heifers than bulls. In all cattle there will be elevated serum concentrations of cortisol from 0.5 to 8 hours, TNF-α from 1 to 2.5 hours, IL-6 from 2 to 8 hours, and IFN-γ from 2.5 to 7 hours after LPS challenge. Additionally, serum concentrations of TNF-α are expected to be greater in heifers than bulls from 1.5 to 2 hours after the LPS challenge. Concentrations of IFN-γ tend to also be greater on average in bulls than heifers. Leukopenia occurred from 1 to 8 hours, with a decreased neutrophil to lymphocyte ratio for the first 5 hours among all calves. These data demonstrate the existence of a sexually dimorphic acute-phase response in pre-pubertal calves. Specifically, heifers may have a more robust acute response to LPS challenge, even though bulls display more signs of sickness.

This trial measures inflammatory response after LPS challenge as a measure of the animal's disease state and state of improvement. For example, compared to the control group of cattle, cattle fed with the feed composition of the present invention showed better DMI(dry matter intake), ADG (average daily gain), lower rectal temperature, lower Cortisol levels, and lower levels of inflammatory cytokines, glucose metabolism and lower NEFA (plasma nonesterified fatty acids (NEFA), also called free fatty acids) concentrations after LPS challenge, all of which are indications of improved animal health.

EXAMPLE 5

Dust Pneumonia the Mechanism a) Dust includes significant finely pulverized manure and contains bacteria endotoxins
b) Particles less than 4 microns (talcum powder) will settle to the bottom of the lung
c) The body uses Macrophages (a type of white blood cell) to "eat the dust" and clear the lung.
d) Endotoxins in the remaining dust damage lung cells and set off moderate to severe AIP and bacterial pneumonias.

Dust Pneumonia Developing Pulls
a) As dusty conditions persist, some cattle fail to completely eliminate the dust and develop low grade infections
b) (Dust Respiratory Pulls).
c) Because the animal's immune system has been continuously stimulated by bacteria, some animals' immune system will have a massive reaction (hypersensitivity from inflammatory cytokines).
d) The surrounding lung tissue and spaces between the lung tissues (interstitial space) will fill with fluid and reactive white blood cells.
e) This is atypical interstitial pneumonia (AIP).
f) Along with dust and bacteria, the animal's immune response adds to the acute severe life threatening symptoms.

Dust Pneumonia Yard
PreventionOTC Yard Run is aimed at stopping growth of developing low grade bacterial pneumonia.
Typical Cost:
a) $0.14/Hd/Day (1.9 Grams)×5 Days=$0.70/Hd
b) Macrophages can "catch up".
c) Reduces overstimulation of immune system.
d) Due to recent FDA rulings OTC is no longer part of our toolbox.

Dust Run Alternative
a) Pre-Vent
b) Cost: 1.5 grams×7 days=$0.70
c) Reduce Bacteria
d) Existing Macrophages "eat more and faster"
e) Directly Stimulates Macrophage Phagocytosis Increases Production of Macrophages.

Reduce Inflammatory Cytokines
a) "Banamine" affect.
b) Avoid destruction of tissue
c) Lower Inflammatory cytokines
d) Lower cortisol
e) Lower body temperatures Response in dust pneumonia without the use of macrolides has also been shown. In cases where the animals do not respond fully to the dust run, when the animals are pulled, the response (effectiveness) of the macrolide is increased, indicating better treatment response.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

What is claimed is:

1. A method for enhancing macrolide antibiotic efficacy in a non-human animal with pneumonia caused by a bacterial infection, the method comprising: (i) selecting a non-human animal with pneumonia; (ii) feeding the non-human animal an effective amount of a non-human animal feed composition comprising isolated or purified beta glucans and mannans for a period of at least about five days before administering a macrolide antibiotic; and (iii) administering the macrolide antibiotic and feeding the feed composition to the non-human animal.

2. The method of claim 1, wherein consuming the effective amount of the feed composition increases the number of lymphocytes of the non-human animal.

3. The method of claim 1, wherein consuming the effective amount of the feed composition increases the number of monocytes of the non-human animal.

4. The method of claim 1, wherein the feed composition further comprises zinc and wherein the zinc is of an amount of no less than about 13,000 ppm by weight.

5. The method of claim 1, wherein the feed composition further comprises protein, wherein the protein is not less than about 10% by weight.

6. The method of claim 1, wherein bacterial infection is caused by *Mannheimia haemolytica, Pasteurella multocida, Mycoplasma bovis, Actinobacillus pleuropneumoniae*, and/or *Histophilu somnus*.

7. The method of claim 1, wherein consuming the effective amount of the feed composition increases the activity of monocytes of the non-human animal.

8. The method of claim 1, wherein the non-human animal is not pulled a second time.

9. The method of claim 8, wherein there is no recurrence of pneumonia to induce a second pull in the non-human animal.

10. A method of treating pneumonia in a vertebrate animal, the method comprising (i) selecting a non-human animal with pneumonia caused by a bacterial infection; (ii) feeding the non-human animal an effective amount of a non-human animal feed composition comprising isolated or purified (1,3) beta glucans, (1,6) beta glucans, and mannans for a period of at least about five days before administering a macrolide antibiotic; and (iii) administering the macrolide antibiotic by injection and feeding the feed composition to the non-human animal.

11. The method of claim 10, wherein the animal is selected from a bovine, porcine, equine, caprine, ovine, hircine, canine, feline, avian, and fowl.

12. The method of claim 10, wherein treating pneumonia comprises a reduction in the number of second or later illnesses or second pulls, or repeat pulls.

13. The method of claim 10, wherein the effective amount of the feed composition comprises an amount of isolated or purified (1,3) and (1,6) beta-glucan from about 2.4 g to about 3.6 g per head per day, and wherein the animal is a cow or cattle.

14. The method of claim 10, wherein the effective amount of the feed composition comprises an amount of (1,3) and/or (1,6) beta-glucan from about 7 mg to about 13 mg per lb. per day, wherein the animal is a swine.

15. The method of claim 10, wherein a combination of (1,3) and (1,6) beta-glucans are in a ratio ranging from 10:1 to 1:10.

16. The method of claim 10, wherein at least one of the mannans, (1, 3) beta-glucans, and (1, 6) beta-glucans is derived from a yeast.

17. The method of claim 10, wherein the pneumonia is atypical interstitial pneumonia.

18. The method of claim 10, wherein the bacterial infection is caused by *Mannheimia haemolytica, Pasteurella multocida, Mycoplasma bovis, Actinobacillus pleuropneumoniae*, and/or *Histophilu somnus*.

19. The method of claim 10, wherein the macrolide antibiotic is selected from tylosin, gamithromycin, tildipirosin, azithromycin, erythromycin, aureomycin, clarithromycin, oleandomycin, roxithromycin, telithromycin, josamycin, mideacamycin, miocamycin, rokitamycin, spiramycin, tildipiromycin, and tylvalosin.

20. The method of claim 10, wherein the macrolide antibiotic is gamithromycin or tildipirosin.

21. The method of claim 10, wherein the macrolide antibiotic is not tilmicosin or tulathromycin.

22. A method for enhancing macrolide antibiotic efficacy in a non-human animal with pneumonia caused by a bacterial infection, the method comprising: (i) feeding the non-human animal an effective amount of a non-human animal feed composition comprising isolated or purified beta glucans and mannans for a period of about five days to about 30 days before administering the macrolide antibiotic; and (ii) administering a therapeutic amount of the macrolide antibiotic and feeding the feed composition to the non-human animal.

23. The method of claim 22, wherein the non-human animal is selected from a bovine, porcine, equine, caprine, ovine, hircine, canine, feline, avian, and fowl.

24. The method of claim 23, wherein the effective amount of the feed composition comprises an amount of isolated or purified (1,3) and (1,6) beta-glucan from about 2.4 g to about 3.6 g per head per day, and wherein the non-human animal is a cow or cattle.

25. The method of claim 23, wherein the effective amount of the feed composition comprises an amount of (1,3) and/or (1,6) beta-glucan from about 7 mg to about 13 mg per lb. per day, wherein the non-human animal is a swine.

26. The method of claim 22, wherein the feed composition further comprises zinc and wherein the zinc is of an amount of no less than about 13,000 ppm by weight.

27. The method of claim 22, wherein the beta glucans comprise a combination of (1,3) and (1,6) beta-glucans in a ratio from 10:1 to 1:10.

28. The method of claim 22, wherein the non-human animal is fed the feed composition for a period of between about 5 days and about 12 days.

* * * * *